(12) United States Patent
Hete

(10) Patent No.: US 11,642,488 B2
(45) Date of Patent: May 9, 2023

(54) VENTILATION SYSTEM WITH COLD PASSOVER HUMIDIFICATION CONTROL

(71) Applicant: KONINKLIJKE PHILIPS N.V., Eindhoven (NL)

(72) Inventor: Bernard Hete, Kittanning, PA (US)

(73) Assignee: Koninklijke Philips N.V., Eindhoven (NL)

( * ) Notice: Subject to any disclaimer, the term of this patent is extended or adjusted under 35 U.S.C. 154(b) by 439 days.

(21) Appl. No.: 16/758,428

(22) PCT Filed: Dec. 18, 2018

(86) PCT No.: PCT/EP2018/085598
§ 371 (c)(1),
(2) Date: Apr. 23, 2020

(87) PCT Pub. No.: WO2019/121749
PCT Pub. Date: Jun. 27, 2019

(65) Prior Publication Data
US 2020/0306492 A1    Oct. 1, 2020

Related U.S. Application Data

(60) Provisional application No. 62/607,348, filed on Dec. 19, 2017.

(51) Int. Cl.
*A61M 16/16* (2006.01)
*A61M 16/00* (2006.01)

(52) U.S. Cl.
CPC ........ *A61M 16/16* (2013.01); *A61M 16/0066* (2013.01); *A61M 2205/14* (2013.01);
(Continued)

(58) Field of Classification Search
CPC .............. A61M 16/0066; A61M 16/16; A61M 2205/14; A61M 2205/18;
(Continued)

(56) References Cited

U.S. PATENT DOCUMENTS 5,722,393 A * 3/1998 Bartel .................... A61M 16/08
128/204.23
5,769,071 A * 6/1998 Turnbull ............... A61M 16/16
128/205.23
(Continued)

FOREIGN PATENT DOCUMENTS

CN    104645469 A    5/2015
CN    206700488 U    12/2017
(Continued)

OTHER PUBLICATIONS

International Search Report for PCT/EP2018/085598 dated Dec. 18, 2018.
(Continued)

*Primary Examiner* — Quynh-Nhu H. Vu
(74) *Attorney, Agent, or Firm* — Daniel H. Brean

(57) ABSTRACT

A ventilation system including a ventilator having a cooling fan configured reduce an internal temperature of the ventilator. The ventilator also includes a controller configured to control operation of the ventilator. A detector is configured to generate a detection signal when the ventilator is connected to a cold passover humidification (CPH) device. In response to the detection signal, the ventilator reduces or eliminates operation of the cooling fan in comparison to a default mode of operation. A method of providing increasing a temperature of a flow of air to a CPH device is also included.

11 Claims, 3 Drawing Sheets

(52) U.S. Cl.
CPC ............ *A61M 2205/3372* (2013.01); *A61M 2205/3561* (2013.01); *A61M 2205/362* (2013.01); *A61M 2205/3606* (2013.01); *A61M 2205/52* (2013.01); *A61M 2205/6063* (2013.01)

(58) Field of Classification Search
CPC ............ A61M 2205/3372; A61M 2205/3561; A61M 2205/3606; A61M 2205/362; A61M 2205/3666
See application file for complete search history.

(56) References Cited

U.S. PATENT DOCUMENTS

| | | | |
|---|---|---|---|
| 6,349,724 B1* | 2/2002 | Burton | F04D 29/052 |
| | | | 128/204.22 |
| 6,584,972 B2* | 7/2003 | McPhee | A61M 16/109 |
| | | | 128/203.17 |
| 7,157,035 B2* | 1/2007 | Edirisuriya | A61M 16/0816 |
| | | | 264/320 |
| 7,306,205 B2* | 12/2007 | Huddart | A61M 16/1075 |
| | | | 128/203.14 |
| 7,983,542 B2* | 7/2011 | McGhin | A61M 16/1075 |
| | | | 392/485 |
| 8,528,552 B2* | 9/2013 | von Blumenthal | A61M 16/026 |
| | | | 128/203.26 |
| 9,649,459 B2 | 5/2017 | Brambilla et al. | |
| 10,143,821 B2 | 12/2018 | Pujol | |
| 10,441,740 B2* | 10/2019 | Mcauley | A61M 16/109 |
| 11,491,291 B2* | 11/2022 | Oldfield | A61B 5/087 |
| 2001/0017134 A1 | 8/2001 | Bahr | |
| 2005/0076906 A1* | 4/2005 | Johnson | A61M 16/0051 |
| | | | 128/204.21 |
| 2008/0053441 A1* | 3/2008 | Gottlib | A61M 16/12 |
| | | | 128/204.23 |
| 2013/0228180 A1 | 9/2013 | Ahmad et al. | |
| 2015/0174344 A1* | 6/2015 | Minocchieri | A61M 11/02 |
| | | | 128/200.23 |
| 2018/0280644 A1* | 10/2018 | Hermez | A61M 16/16 |
| 2019/0372369 A1 | 12/2019 | Blunsden et al. | |

FOREIGN PATENT DOCUMENTS

| | | |
|---|---|---|
| WO | 200113981 A1 | 3/2001 |
| WO | 2010146870 A1 | 12/2010 |

OTHER PUBLICATIONS

Koshimaa, M. et al., "Heat and moisture retention in breathing gas during mechanical ventilation". Vital Signs a GE Healthcare Company. ACC-0383-04.13-EN-US, L2158_v1_April 2013. DOC1310042.
Branson, R.D. et al., "Is humidification always necessary during noninvasive ventilation in the hospital?" Respiratory Care. Feb. 2010, vol. 55, No. 2, p. 209-216.

* cited by examiner

VENTILATION SYSTEM WITH COLD PASSOVER HUMIDIFICATION CONTROL

CROSS-REFERENCE TO PRIOR APPLICATIONS

This application claims the priority benefit under 35 U.S.C. § 371 of International Patent Application No. PCT/EP2018/085598, filed on Dec. 18, 2018, which claims the priority benefit of U.S. Provisional Patent Application No. 62/607,348, filed on Dec. 19, 2017, the contents of which are herein incorporated by reference.

FIELD OF THE INVENTION

The present disclosure is directed generally to medical ventilation systems, more particularly, ventilation systems including cold passover humidification devices to humidify the flow of air to a patient.

BACKGROUND

Cold passover humidification (CPH) is a known method for humidifying ventilation gas where the ventilator output flow passes over a water surface to pick up water vapor. The method is referred to as "cold passover humidification" because it humidifies the air without the addition of heat energy to the water. An advantage to using CPH in ventilation systems is that it operates without power or a designated heater, in addition to being relatively simple and inexpensive to manufacture and operate in comparison to other humidifying techniques.

However, the lack of a designated heater results in a tradeoff in that CPH has a relatively limited ability to humidify the flow of air. That is, since no heat is added, any evaporation occurs as a result of heat transferred from the flowing airstream to the water in the CPH device. The amount of humidification achieved by a CPH process is thus limited in a variety of ways. For example, room temperature air is capable of holding far less water than body temperature air. Also, as water evaporates, it cools the surface from which it leaves, which causes cooling of the contacting air stream, thereby further reducing the moisture-holding ability of the water, while also presenting the patient with a relatively cooler airstream, which may not be desired. Additionally, the evaporation of water is energy intensive and because air has a generally poor heat capacity, it is not generally a good medium for transferring energy for this process.

Accordingly, there is a need in the art for ventilation systems that provide improved levels of humidification while enjoying the relative cost, simplicity, and operational benefits of CPH.

SUMMARY OF THE INVENTION

The present disclosure is directed to inventive systems and methods for humidifying air, for example, during ventilation to a patient. Methods of the present disclosure include detecting whether a ventilator is connected to a CPH device with a detector. In response to a signal indicative of detection of the CPH device, a controller of the ventilator reduces or eliminates operation of a cooling fan of the ventilator in comparison to a default mode of operation. The reduction or elimination of operation of the cooling fan results in a relative increase in the internal temperature of the ventilator, which in turn, increases the temperature of the air flow generated to the patient that is generated by the ventilator. The increase in air flow temperature enables an increased level of humidification to occur when the air flow passes through a chamber of the CPH device.

Generally, in one aspect, a ventilation system is provided. The system includes a ventilator having a cooling fan configured to reduce an internal temperature of the ventilator; a controller (30) configured to control operation of the ventilator; and a detector (36) configured to generate a detection signal when the ventilator is connected to a cold passover humidification (CPH) device (14); wherein in response to the detection signal, the controller is configured to modulate, reduce, or eliminate operation of the cooling fan in comparison to a default mode of operation of the ventilator.

In one embodiment, the detector includes a communication device enabling the ventilator to establish communication with the CPH device over a communication link. In one embodiment, the communication device includes one or more communication ports of the ventilator and the communication link includes a cable connected between the ventilator and the CPH device. In one embodiment, the communication device includes a transmitter, receiver, or radio and the communication link includes wireless communication.

In one embodiment, the detector includes a sensor that is arranged to detect a feature of a conduit specific to the CPH device. In one embodiment, the cooling fan is always running when in the default mode of operation. In one embodiment, the cooling fan operates at a relatively higher speed in the default mode of operation than after the controller modules, reduces, or eliminates operation of the cooling fan. In one embodiment, the cooling fan is turned off in response to the detection signal.

In one embodiment, the ventilator is configured such that there are a range of the internal temperatures at which the cooling fan would have operated in the default mode but at which the cooling fan does not operate after the ventilator modulates the operation of the cooling fan. In one embodiment, the ventilator further comprises a temperature sensor (52) that monitors the internal temperature of the ventilator. In one embodiment, the internal temperature corresponds to one of more electrical or mechanical components within the ventilator, a volume of air surrounding the one or more electrical or mechanical components, or a combination including at least one of the foregoing.

According to one aspect, a method for operating a ventilation system having a cold passover humidification (CPH) device is provided. The method comprises the steps of detecting whether a ventilator is connected to the CPH device; generating a detection signal in response to the detecting; changing the ventilator from a default mode of operation in response to the detection signal; and reducing or eliminating operation of a cooling fan of the ventilator in comparison to the default mode of operation as a result of the step of changing.

In one embodiment, the method further includes generating an air flow with an air flow generator of the ventilator; and directing the air flow to the CPH device. The method may further comprise a step of receiving the detection signal with a controller of the ventilator and the step of changing is performed by the controller. In one embodiment, the step of detecting is performed by a detector and the detector comprises a communication device of the ventilator or of the CPH device, a cable, a communication port, a transceiver, a receiver, a radio, a sensor, a feature of a conduit specific to the CPH device, or a combination including at least one of the foregoing.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of a ventilation system and methods for operating the ventilation system. More generally, Applicant has recognized and appreciated that it would be beneficial to provide a ventilation system having a detector that detects when a ventilator is connected with a cold passover humidification (CPH) device and to adjust operation of the ventilator when so connected. A particular goal of certain embodiments of the present disclosure is to increase the temperature of an air flow provided by a ventilator to a CPH device, without the need for an additional heater.

In view of the foregoing, various embodiments and implementations are directed to system and methods for humidifying air, for example, during ventilation to a patient. Methods of the present disclosure include detecting whether a ventilator is connected to a CPH device with a detector. In response to a signal indicative of detection of the CPH device, a controller of the ventilator reduces or eliminates operation of a cooling fan of the ventilator in comparison to a default mode of operation. The reduction or elimination of operation of the cooling fan results in a relative increase in the internal temperature of the ventilator, which in turn, increases the temperature of the air flow generated to the patient that is generated by the ventilator. The increase in air flow temperature enables an increased level of humidification to occur when the air flow passes through a chamber of the CPH device.

Figure 1:
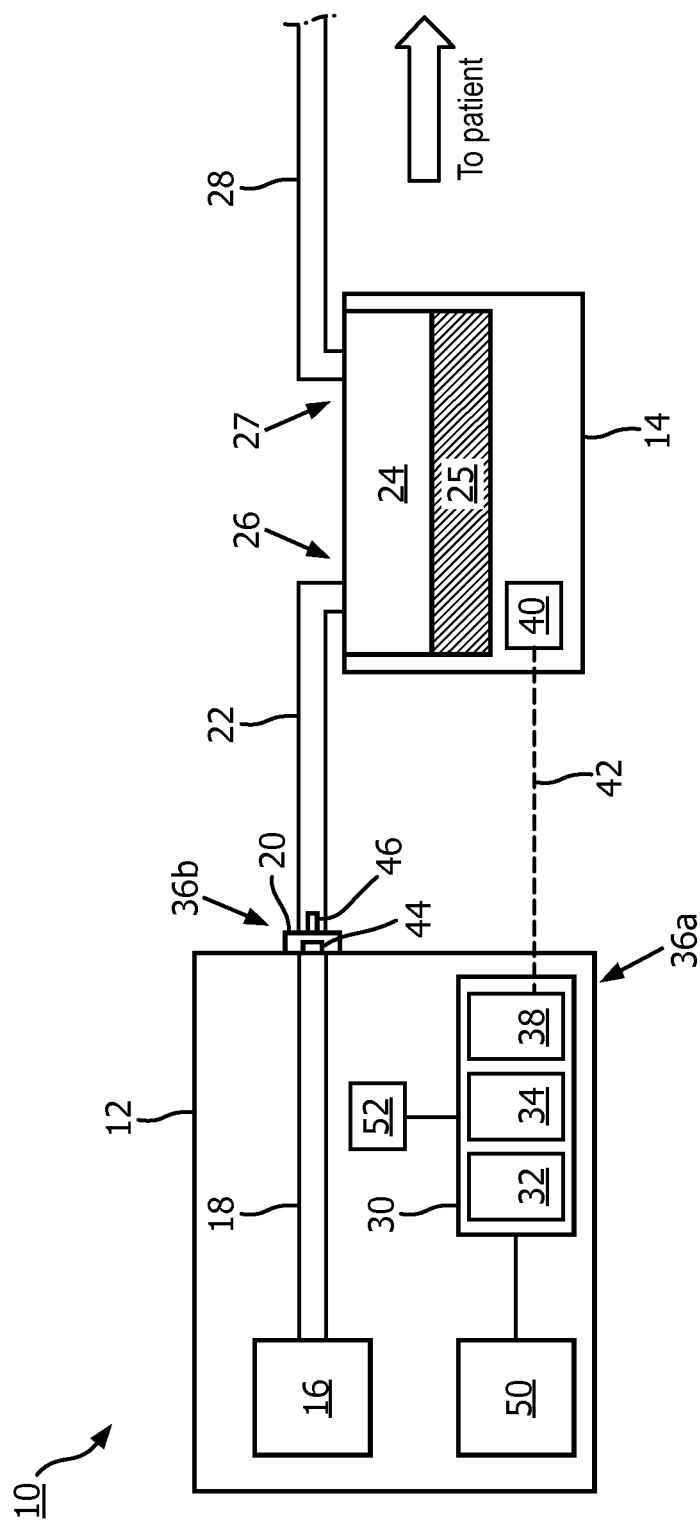
FIG. 1 schematically illustrates a ventilation system according to one embodiment disclosed herein.

Referring to FIG. 1, in one embodiment, a ventilation system 10 is provided with a ventilator 12 and a cold passover humidification (CPH) device 14. The ventilator 12 includes an air flow generator 16 that provides a pressurized flow of air via a channel 18 in the ventilator 12 to an outlet 20 of the ventilator 12. The outlet 20 is connected to a conduit (or tubing) 22 that is coupled between the ventilator 12 and the CPH device 14. The air flow generator 16 may be any device or mechanism for providing the flow of air. For example, in one embodiment the air flow generator 16 includes a pump or fan that is powered by a motor.

It is to be understood that the term "air" as used herein and in the claims refers to any breathable mixture of gases provided to the patient via the system 10. This breathable mixture of gases, and thus "air" as referred to herein, may include gaseous components or substances not naturally found in the ambient environment, or components or substances in different percentages than those naturally found (e.g., higher percentages of oxygen, helium, etc.) that are useful to assist in various treatments or procedures with the ventilator 12.

In general, the CPH device 14 includes an air chamber 24 that is open to a volume of water 25 to permit evaporation of the water into the air (humidification of the air flow). In the context of the instant disclosure, by "water" it is meant any aqueous mixture that is desired to add humidity to the air flow. An inlet 26 of the CPH device is connected to the conduit 22 and directs the air flow into the air chamber 24. An outlet 27 of the CPH device 14 is connected to a conduit (or tubing) 28, which ultimately leads to a patient. In this way, a pathway is formed for the flow of air from the air flow generator 16 through the channel 18, outlet 20, conduit 22, inlet 26, air chamber 24, outlet 27, and conduit 28 to the patient, i.e., to assist the patient in breathing utilizing the flow of air. The CPH device 14 can include any combination of other features, forms, or functionality of any CPH device known or discovered in the art.

The ventilator 12 includes a controller 30 that is arranged to control the operation of the ventilator 12. For example, the controller 30 may include computer hardware such as a processor 32 configured to execute software such as programming code or other instructions, and a memory 34 for storing data, or information, such as the aforementioned software. The controller 30 can be arranged to provide the features of any ventilator known or discovered in the art. In addition, the controller 30 is configured to receive a signal that indicates that the ventilator 12 is connected to the CPH device 14 and to control operation of the ventilator 12 in response to this signal, as discussed in more detail below.

Ventilators such as the ventilator 12 are typically usable for a variety of different procedures and are thus designed to be connectable to a patient with or without the inclusion of a selection of auxiliary devices such as cold passover humidifiers. Thus, the system 10 includes a detector (or CPH detector) that is arranged to detect whether the ventilator 12 is connected to the CPH device 14, as opposed to connected directly to a patient or other device. Various embodiments of CPH detectors are disclosed herein and illustrated in the drawings and may be provided with the reference numeral 36 appended with an alphabetic identifier (i.e., 'a', 'b', etc.) to enable individual embodiments to be easily identified for discussion. It is to be appreciated that any description made with reference to the "detector(s) 36" or "the CPH detector(s) 36" (without an alphabetic identifier) is applicable generally to any/all of the detectors disclosed herein.

FIG. 1 discloses various embodiments for the CPH detector. In one embodiment, a CPH detector 36a includes a communication device 38 that is part of, or otherwise connected in communication with, the controller 30 of the ventilator 12. The communication device 38 may be any component, device, assembly, or apparatus that is arranged to permit communication between the ventilator 12 and the CPH device 14, e.g., via a communication device 40 of the CPH device 14, as indicated by a communication link 42.

The communication device 40 may include a processor, memory, etc. and be additionally arranged as, or connected to, a controller to enable and/or facilitate operation of the CPH device 14 if desired.

In one embodiment, the communication device 38 may be or include one or more communication ports provided on the ventilator that are coupled or able to be coupled to a cable that is or can be similarly coupled to the CPH device 14 to enable signal communication between the controller 30 of the ventilator 12 and the communication device 40 of the CPH device 14. In this embodiment, the communication link 42 may thus be physically formed by a cable or other "wired" connection. In one embodiment, the communication device 38 may include a transmitter, receiver, radio, or other wireless communication device arranged to permit the ventilator 12 to communication wirelessly with the CPH device 14. Thus, the communication link 42 in this embodiment would be or include a wireless connection. Examples of technologies/protocols that could be used to create a wireless connection include RFID, Bluetooth, Wi-Fi, near-field communication, etc. In these embodiments for the detector 36a, the controller 30 may be arranged to detect the identity of the communication device 40 and recognize it as corresponding to the CPH device 14, the controller 30 may be configured to send a signal to the communication device 40 requesting it to provide the identity of the communication device 40 and/or the CPH device 14, and/or the controller 30 may be arranged to receive a signal from the communication device 40 "announcing" the presence and identity of the communication device 40 and/or the CPH device 14.

FIG. 1 also illustrates a CPH detector 36b according to one embodiment. The detector 36b includes a sensor 44 that is included proximate to the outlet 20 (e.g., embedded with, adjacent, or in the vicinity of the outlet 20). The sensor 44 is arranged to detect the presence and identity of conduits connected to the outlet 20 to differentiate between different types of conduits. In this embodiment, it is thus assumed different conduits are intended to be used for different purposes, e.g., the conduit 22 is only intended to connect to the CPH device 14. In other words, the conduit 22 in this embodiment is specific to the CPH device 14. To this end, the conduit 22 includes a feature 46 that is detectable by the sensor 44 and unique to the conduit 22 (e.g., the conduit 28 does not include the feature 46, and thus, would not be detected by the sensor 44). In this way, the sensor 44 is configured to detect the feature 46 that is unique to the conduit 22, which in turn is unique to the CPH device 14, and to accordingly send a signal to the controller 30 if this unique feature 46 is identified, which indicates that the CPH device 14 is connected to the ventilator 12.

In one embodiment, the sensor 44 is a Hall effect sensor, reed switch, etc. that is responsive to changes in magnetic fields and the feature 46 is or includes a magnetic element (e.g., magnet or ferrite) that is identifiable by the sensor 44. In this embodiment, other conduits, e.g., the conduit 28, would not include a magnetically responsive element, and thus, would not be detected by the sensor 44. In another embodiment, the sensor 44 includes a physical switch, button, lever, etc. and the feature 46 includes a protrusion or physical geometry that corresponds to and is aligned with the sensor 44 to physically trigger the sensor 44 when the conduit 22 is attached to the outlet 20. In one embodiment, the sensor 44 and the feature 46 include corresponding electrical components that enable wireless technology such as RFID. In one embodiment, the sensor 44 and the feature 46 include electrical contacts that are aligned and engaged to generate a signal when the conduit 22 is connected to the outlet 20.

In view of the disclosure herein, those of ordinary skill in the art will recognize that these are but some of the possible embodiments, and that there exist alternate and additional ways in which the ventilator 12 may be arranged to detect whether or not it is connected to the CPH device 14. Furthermore, it is to be understood that while the system 10 in FIG. 1 is illustrated with both the detectors 36a and 36b, that only one of these detectors (or an alternate detector according to a non-illustrated embodiment) needs to be included for the CPH detection signal to be received by the controller 30. Of course, multiple ones of the detectors 36 may be included by the ventilator 12 for redundancy and/or to correspond to detect the unique features of different models/manufacturers of CPH devices.

As noted above, the controller 30 is arranged to control operation of the ventilator 12 in response to the controller 30 receiving the signal from the detector 36 that is indicative of the ventilator 12 being connected to the CPH device 14. More specifically, the ventilator 12 includes a cooling fan 50 that is controlled in response to the controller 30 receiving the CPH detection signal. The cooling fan 50 is arranged for reducing the internal temperature of the ventilator 12, e.g., by forcing out heat generated by electrical and/or mechanical components of the ventilator 12. For example, electrical components, such as the processor 32, or mechanical components, such as a motor of the air flow generator 16, may create a significant amount of waste heat during operation. The cooling fan 50 can be arranged to exhaust this waste heat from the ventilator 12, thereby cooling the components of the ventilator 12 and reducing an internal temperature of the ventilator 12.

A temperature sensor 52 may be included to measure the internal temperature of the ventilator 12. The temperature sensor 52 may measure air temperature, e.g., of a volume of air surrounding the controller 30 or other electrical or mechanical components of the ventilator 12. Additionally or alternatively, the temperature sensor 52 may measure the temperature of particularly critical or sensitive components of the ventilator 12, e.g., the processor 32. In one embodiment, a plurality of the temperature sensors 52 is included for measuring the internal temperature of the ventilator 12 at multiple different locations/components.

Figure 2:
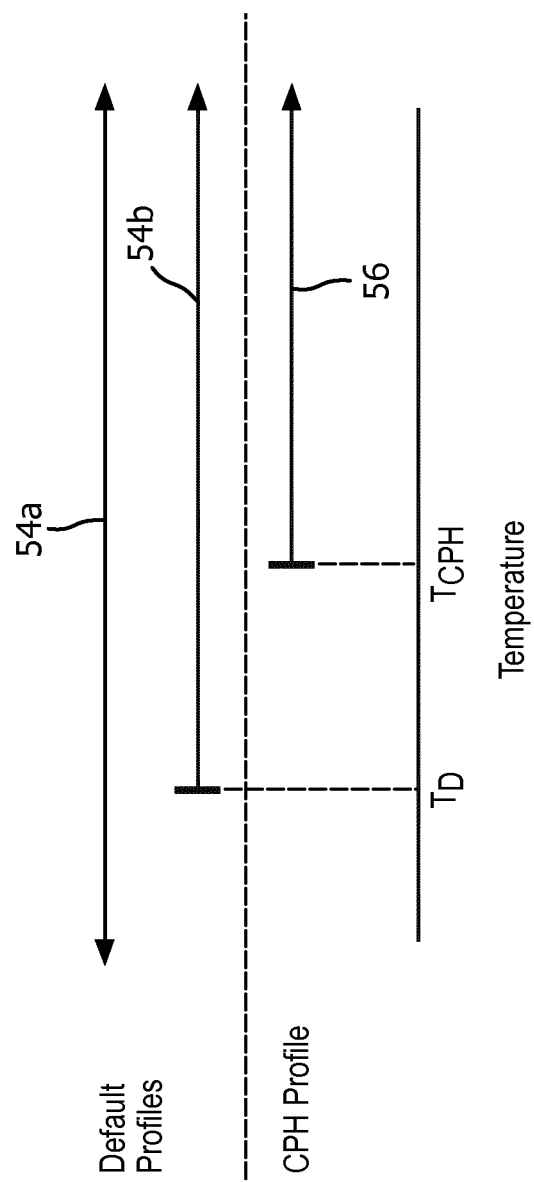
FIG. 2 schematically illustrates a comparison of modes of operation for a cooling fan of a ventilator system, such as the system of FIG. 1.

In response to the detection signal being received by the controller 30 from the detector 36, the controller 30 is arranged to modulate operation of the ventilator 12 and/or cooling fan 50 by changing the mode of operation from a default mode of operation to another mode of operation (hereinafter a "CPH mode"). In one embodiment, this results in operation of the cooling fan 50 being reduced or eliminated in comparison to the default mode of operation. FIG. 2 is provided to assist in describing the difference between the operational modes for the cooling fan 50. A first default mode, represented by an arrow 54a, a second default mode, represented by an arrow 54b, and a CPH mode, represented by an arrow 56, are illustrated in FIG. 2. For convenience in discussion, each mode of operation may be referred to by the reference numeral of the arrow representing that mode.

In one embodiment, the arrows 54a, 54b, and 56 in FIG. 2 extend over the range of temperatures of the ventilator 12 (e.g., as measured by the temperature sensor 52) at which the cooling fan 50 operates (i.e., is turned on) when in the corresponding mode of operation. In one embodiment, the arrows 54a, 54b, and 56 extend over the range of temperatures at which the cooling fan transitions from a first performance level, speed, or setting (e.g., "off" or "low") to a second performance level, speed, or setting that is relatively more effective (e.g., "on" or "high").

As indicated in FIG. 2, the first default mode 54a corresponds to an "always on" operational mode in which the cooling fan 50 is always running, regardless of the internal temperature of the ventilator 12 (provided the ventilator 12 is turned on). The second default mode 54b differs in that the cooling fan 50 transitions between performance levels (e.g., on and off, or high and low) only at temperatures above a default threshold temperature $T_D$. In other words, the cooling fan 50 only turns on, or changes to a higher speed setting, when the internal temperature of the ventilator 12 becomes too high.

The CPH mode 56 is similar to the default mode 54b, in that it results in the cooling fan 50 transitioning between different performance levels at a CPH threshold temperature $T_{CPH}$. However, it can be seen in FIG. 2 that the CPH threshold temperature $T_{CPH}$ is greater than the default threshold temperature $T_D$. This results in a range of temperatures at which the cooling fan 50 would have operated if in one of the default operational modes, but which it does not when operating in accordance with the CPH mode 56. Thus, the range is any temperature, T, less than $T_{CPH}$ with respect to the first default mode 54a ($T<T_{CPH}$), or any temperature, T, between $T_D$ and $T_{CPH}$ with respect to the second default mode 54b ($T_D<T<T_{CPH}$). In other words, in response to the CPH detection signal, the controller 30 purposely reduces or eliminates operation of the cooling fan 50 in comparison to operation of the cooling fan 50 during its default mode of operation (either of the default modes 54a or 54b).

The reduction or elimination of operation of the cooling fan 50 causes the internal temperature of the ventilator 12 (e.g. as measured by the temperature sensor 52) to increase. This increase in internal temperature correspondingly increases a temperature of the air within the channel 18. For example, if the cooling fan 50 and other components are segregated or isolated from the air generator 16 and the channel 18, then the walls of the channel 18 will effectively enable the ventilator 12 to act as a heat exchanger, providing excess heat (from the reduction or elimination of operation of the cooling fan 50) to the air in the channel 18 through the walls of the channel 18. Additionally, the ventilator 12 will increase the ambient air immediately adjacent to the ventilator 12, which is drawn into the ventilator 12 via the air flow generator 16. As a result, the air that reaches the chamber 24 of the CPH device 14 will be relatively warmer when operating the cooling fan 50 via the CPH mode 56 than it would be if using either of the default modes 54a or 54b. This warmer air will have both an increased capacity to hold moisture and an increased amount of energy with which to drive evaporation from the water 25. Advantageously, this warmer air is achieved without the need for an additional heater or power supply.

By including the detector 36, it is ensured that the operation of the cooling fan 50 is only reduced or eliminated when the ventilator 12 is connected to the CPH device 14. In this way, the ventilator 12 may operate according to its default operational mode when other devices are connected to the ventilator 12, such that the ventilator 12 can continue to be used as expected for different procedures using any number of devices other than the CPH device 14. In one embodiment, the software of an existing ventilator's controller is updated to retrofit that ventilator to operate in accordance to the embodiments disclosed herein. In such retrofit embodiments, hardware components corresponding to the detectors 36 may additionally need to be added (e.g., if the ventilator does not include a communication device similar to the communication device 38 or sensor similar to the sensor 44). In retrofit embodiments, it is noted that since CPH devices are much less complex and expensive than medical ventilators, it may be advantageous to include hardware components of the detector 36 (e.g., sensors such as the sensor 44) with the CPH device as opposed to the ventilator.

Figure 3:
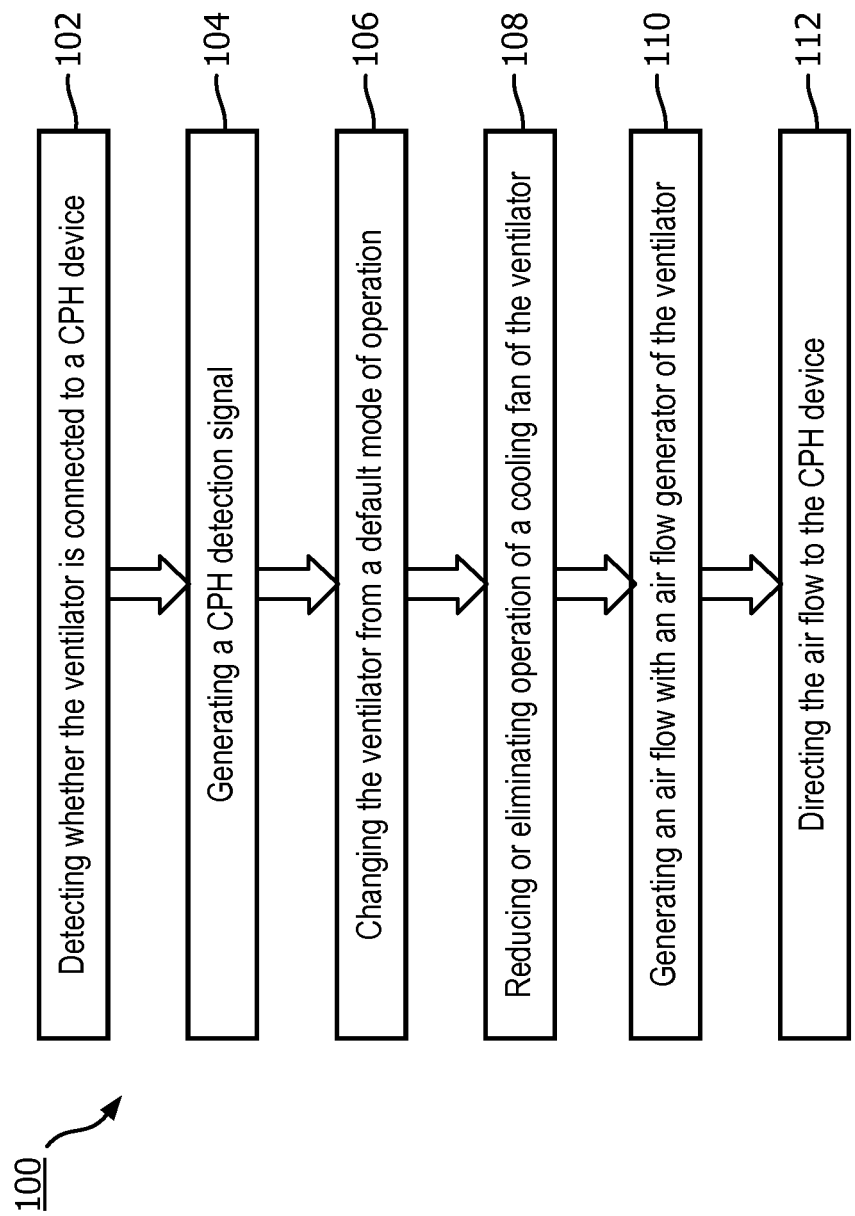
FIG. 3 schematically illustrates a method of operating a ventilator system, such as the system of FIG. 1.

In addition to the disclosure above, a method 100 for operating a ventilation system, e.g., the system 10, can be appreciated in view of FIG. 3. At a step 102, it is detected whether a ventilator, e.g., the ventilator 12, is connected to a CPH device, e.g., the CPH device 14. As discussed above with respect to the detector 36, this can be accomplished in a variety of ways. At a step 104, a CPH detection signal is generated, e.g., by the detector 36. The detection signal may be received by a controller of the ventilator, e.g., the controller 30 of the ventilator 12.

Next, at a step 106, the ventilator is changed from a default mode of operation in response to generation of the CPH detection signal. The default modes 54a and 54b are described above. As a result of the change in the mode of operation of the ventilator, the operation of a cooling fan of the ventilator, e.g., the cooling fan 50, is reduced or eliminated at a step 108. The mode 56 is described above and it is detailed how operation of the cooling fan 50 may be reduced or eliminated to increase the internal temperature of the ventilator 12 in comparison to what would have happened if the ventilator 12 were operated in accordance with its default modes 54a and 54b.

The ventilator may at a step 110 generate an air flow with an air flow generator, e.g., the air flow generator 16. Lastly, the air flow is directed from the ventilator to the CPH device at a step 112 where it can undergo humidification in the CPH device. The humidified air flow can then be directed to a patient.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A ventilation system comprising:
   a ventilator having a cooling fan configured to reduce an internal temperature of the ventilator;
   a controller configured to control operation of the ventilator;
   a cold passover humidification (CPH) device; and
   a detector configured to detect whether the ventilator is connected to the cold passover humidification (CPH) device and generate a detection signal when responsive to detecting the ventilator is connected to the (CPH) device;
   wherein in response to the detection signal, the controller is configured to modulate, reduce, or eliminate operation of the cooling fan in comparison to a default mode of operation of the ventilator.

2. The ventilation system of claim 1, wherein the detector includes a communication device enabling the ventilator to establish communication with the CPH device over a communication link.

3. The ventilation system of claim 2, wherein the communication device includes one or more communication ports of the ventilator and the communication link includes a cable connected between the ventilator and the CPH device.

4. The ventilation system of claim 2, wherein the communication device includes a transmitter, receiver, or radio and the communication link includes wireless communication.

5. The ventilation system of claim 1, wherein the detector includes a sensor that is arranged to detect a feature of a conduit specific to the CPH device.

6. The ventilation system of claim 1, wherein the cooling fan is always running when in the default mode of operation.

7. The ventilation system of claim 1, wherein the cooling fan operates at a relatively higher speed in the default mode of operation than after the controller modules, reduces, or eliminates operation of the cooling fan.

8. The ventilation system of claim 1, wherein the cooling fan is turned off in response to the detection signal.

9. The ventilation system of claim 1, wherein the ventilator is configured such that there are a range of the internal temperatures at which the cooling fan would have operated in the default mode but at which the cooling fan does not operate after the ventilator modulates the operation of the cooling fan.

10. The ventilation system of claim 1, wherein the ventilator further comprises a temperature sensor that monitors the internal temperature of the ventilator.

11. The ventilation system of claim 1, wherein the internal temperature corresponds to one of more electrical or mechanical components within the ventilator, or a volume of air surrounding the one or more electrical or mechanical components.

* * * * *